United States Patent
Daamen et al.

(10) Patent No.: US 9,891,183 B2
(45) Date of Patent: Feb. 13, 2018

(54) BREACH SENSOR

(71) Applicant: NXP B.V., Eindhoven (NL)

(72) Inventors: Roel Daamen, Herkenbosch (NL); Viet Hoang Nguyen, Leuven (NL); Nebojsa Nenadovic, Nijmegen (NL); Pascal Bancken, Leuven (BE)

(73) Assignee: NXP B.V., Eindhoven (NL)

( * ) Notice: Subject to any disclaimer, the term of this patent is extended or adjusted under 35 U.S.C. 154(b) by 152 days.

(21) Appl. No.: 14/793,257

(22) Filed: Jul. 7, 2015

(65) Prior Publication Data
US 2017/0010232 A1   Jan. 12, 2017

(51) Int. Cl.
| | |
|---|---|
| *G01N 27/24* | (2006.01) |
| *G01N 27/22* | (2006.01) |
| *G06F 21/87* | (2013.01) |
| *H01L 23/00* | (2006.01) |
| *G01N 21/88* | (2006.01) |

(52) U.S. Cl.
CPC ....... *G01N 27/223* (2013.01); *G01N 21/8851* (2013.01); *G01N 27/24* (2013.01); *G06F 21/87* (2013.01); *H01L 23/57* (2013.01); *G01N 2021/8854* (2013.01)

(58) Field of Classification Search
CPC .. G01N 27/223; G01N 21/8851; G01N 27/24; G01N 2021/8854; G06F 21/87; H01L 23/57
USPC .................. 73/29.01; 380/4; 257/71; 365/53
See application file for complete search history.

(56) References Cited

U.S. PATENT DOCUMENTS

| | | | |
|---|---|---|---|
| 3,943,557 A | 3/1976 | Frazee et al. | |
| 5,053,992 A * | 10/1991 | Gilberg | G06F 21/87 257/922 |
| 5,159,629 A * | 10/1992 | Double | G06F 21/87 206/807 |
| 5,998,858 A | 12/1999 | Little et al. | |
| 7,482,924 B1 * | 1/2009 | Beinhocker | G08B 13/186 250/227.14 |
| 7,675,066 B1 * | 3/2010 | Dougherty | G06F 21/79 257/71 |
| 7,880,248 B1 * | 2/2011 | Pham | H01L 23/573 257/417 |

(Continued)

FOREIGN PATENT DOCUMENTS

| | | |
|---|---|---|
| EP | 2056346 A2 | 5/2009 |
| KR | 20050066558 A | 6/2005 |

(Continued)

OTHER PUBLICATIONS

Owen, Steve; "Securing Your Smart Life through Trusted Solutions"; presented Innovation Forum 2012; 34 pages.

(Continued)

*Primary Examiner* — Lisa Caputo
*Assistant Examiner* — Nathaniel T Woodward

(57) ABSTRACT

One example discloses a breach sensor, comprising: a substrate including an integrated circuit; a passivation layer coupled to the substrate; a breach sensing element coupled to the circuit; wherein the breach sensing element is on a first side of the passivation layer and the substrate is on a second side of the passivation layer; a barrier configured to separate the breach sensing element from an ambient environment; wherein the breach sensing element is responsive to barrier damage.

19 Claims, 9 Drawing Sheets

(56) References Cited

U.S. PATENT DOCUMENTS

| | | |
|---|---|---|
| 8,896,073 B2 | 11/2014 | Ponomarev et al. |
| 2003/0149914 A1 | 8/2003 | Kim |
| 2004/0031339 A1 | 2/2004 | Swanson et al. |
| 2005/0036383 A1 | 2/2005 | Gamperl et al. |
| 2005/0218465 A1* | 10/2005 | Cummins ............ G01N 27/121 257/414 |
| 2006/0076413 A1 | 4/2006 | Kund et al. |
| 2008/0191716 A1 | 8/2008 | Chen et al. |
| 2009/0013415 A1 | 1/2009 | Lee et al. |
| 2010/0225380 A1 | 9/2010 | Hsu et al. |
| 2012/0151580 A1 | 6/2012 | Chae et al. |
| 2012/0176244 A1* | 7/2012 | Niederhuefner ... G08B 13/1427 340/568.1 |
| 2012/0211845 A1 | 8/2012 | Daamen et al. |
| 2012/0304742 A1 | 12/2012 | Cummins |
| 2013/0314121 A1 | 11/2013 | Mougin et al. |
| 2014/0103286 A1 | 4/2014 | Chu et al. |
| 2014/0103485 A1 | 4/2014 | Fritz et al. |
| 2014/0103957 A1 | 4/2014 | Fritz et al. |

FOREIGN PATENT DOCUMENTS

| | | |
|---|---|---|
| KR | 20120062590 A | 6/2012 |
| WO | 2006/075022 A1 | 7/2006 |
| WO | 2010/028896 A1 | 3/2010 |

OTHER PUBLICATIONS

Sharp, Alastair; "Blackberry works with Boeing on phone that self-destructs"; Reuters; 4 pages Retrieved from the Internet http://www/reuters.com/article/2014/12/19/us-biackberry-boeing-idUSKBNOJXwD020141219 Jun. 29, 2015 (Dec. 19, 2014).

* cited by examiner

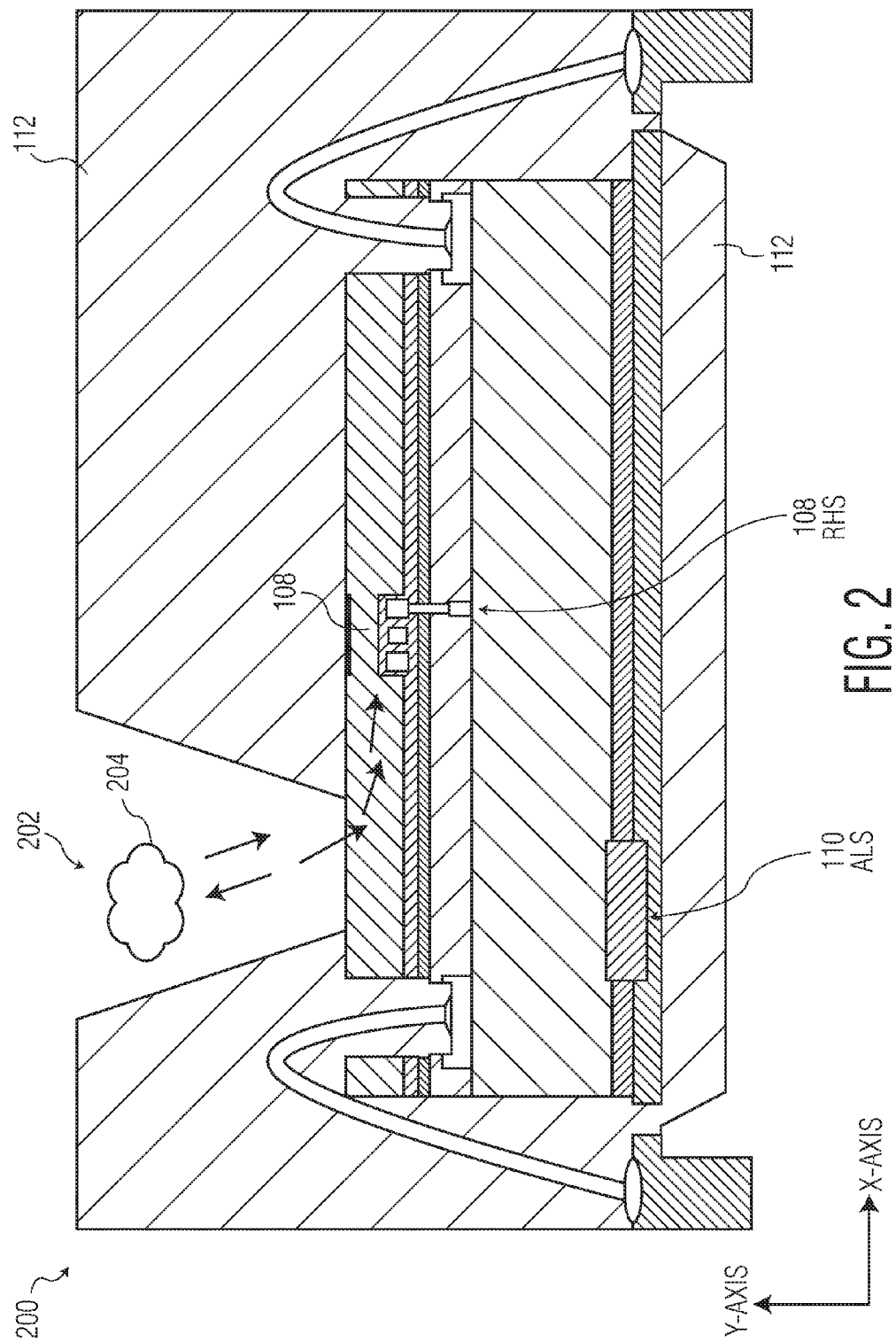

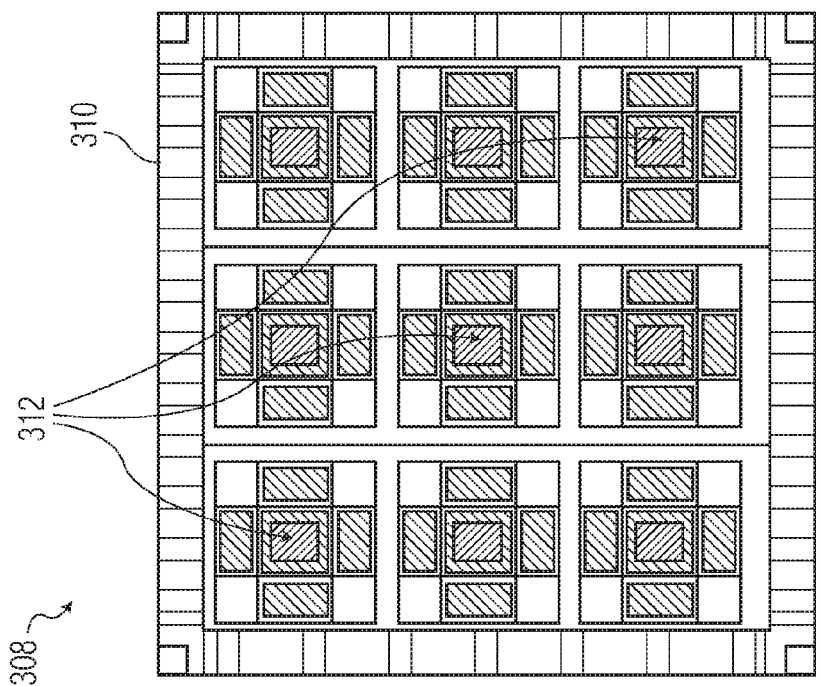
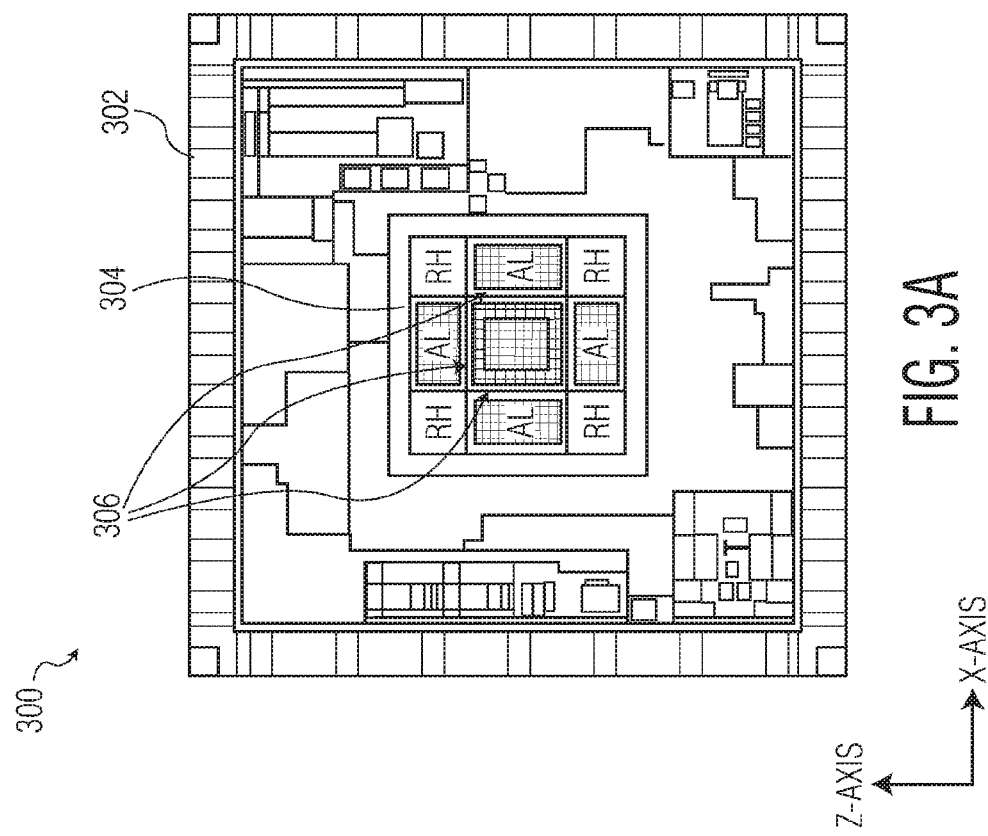
FIG. 3A
FIG. 3B

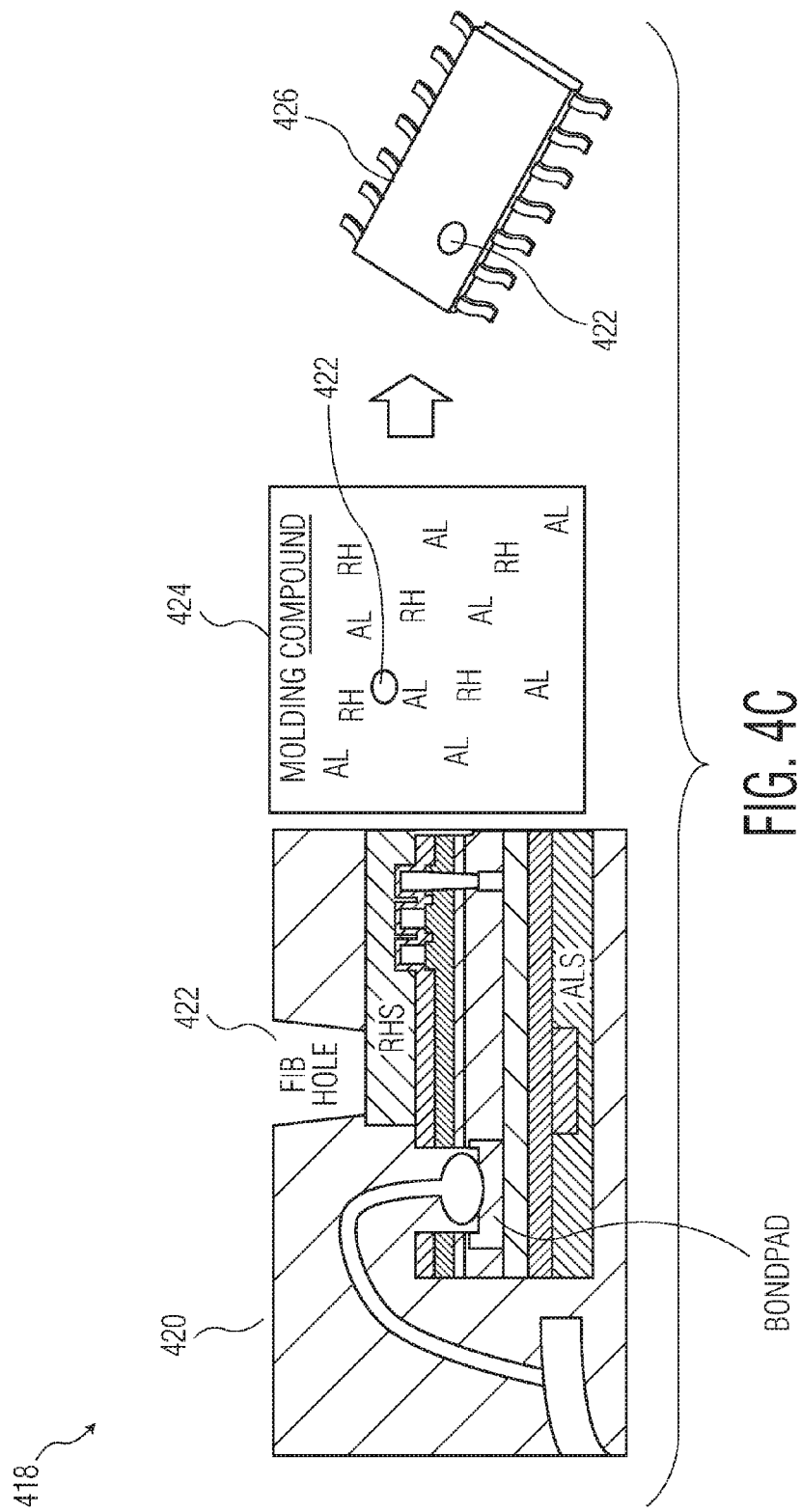

BREACH SENSOR

The present specification relates to systems, methods, apparatuses, devices, articles of manufacture and instructions responsive to package breaches.

Packages can be damaged for a variety of reasons, both benign and not so benign. In a benign example, packages may be designed to be opened whereby the opening process causes predictable and/or intended collateral damage to the package.

However in a not so benign example, integrated circuit chip packages can be damaged due to an intentional physical hacking attack designed to compromise the security features of the integrated circuit. Hacking techniques include: package thinning, FIB (Focused Ion Beam) holes, and de-capping.

In some cases, compromised chips may reveal their proprietary circuit structures and schematics. In other situations, such compromised chips can be powered to either reveal their operation, or reprogrammed to gain access to a secure system, such as a banking server.

SUMMARY

According to an example embodiment, a breach sensor, comprising: a substrate including an integrated circuit; a passivation layer coupled to the substrate; a breach sensing element coupled to the circuit; wherein the breach sensing element is on a first side of the passivation layer and the substrate is on a second side of the passivation layer; and a barrier configured to separate the breach sensing element from an ambient environment; wherein the breach sensing element is responsive to barrier damage.

In another example embodiment, the breach sensing element includes a humidity sensing element configured to detect a humidity level change in response to barrier damage.

In another example embodiment, the humidity sensing element is pre-calibrated with a first humidity level; further comprising a second humidity sensing element pre-calibrated with a second humidity level, different from the first humidity level; and the first and second humidity sensor are separated by a second barrier.

In another example embodiment, the humidity sensor includes at least one of: a capacitive sensing structure or a polyimide.

In another example embodiment, the barrier is directly bonded to the breach sensing element.

In another example embodiment, the barrier includes at least one of: a encapsulation material, a cover, a wrapper, a glue, or a seal.

In another example embodiment, the barrier damage includes at least one of: a focused ion beam hole, a de-capping, a shear, a tear, an etch, or a physical attack.

In another example embodiment, the breach sensor includes a light sensor and the breach sensing element includes a light sensing element configured to detect a photo current change in response to barrier damage.

In another example embodiment, the light sensor includes an avalanche photodiode.

In another example embodiment, the circuit, in response to the barrier damage, is configured to at least one of: damage the circuit, erase a memory, transmit an alert, enter a decoy mode, or blow a fuse.

In another example embodiment, further comprising an antenna coupled to the circuit and configured to transmit a breach signal in response to barrier damage.

In another example embodiment, the breach sensor includes a light sensor and the breach sensing element includes a light sensing element configured to generate power in response to barrier damage.

In another example embodiment, the circuit is coupled to receive the power generated by the light sensor.

In another example embodiment, further comprising a second breach sensor, having a second breach sensing element, proximate to the breach sensor; and the two breach sensors are separated by a second barrier configured to separate the second breach sensing element from the first breach sensing element.

In another example embodiment, the two breach sensors are at least one of: stacked or side-by-side.

According to another example embodiment, an article of manufacture including at least one non-transitory, tangible machine readable storage medium containing executable machine instructions for breach sensing, comprising: wherein the article includes, a substrate including an integrated circuit; a passivation layer coupled to the substrate; a breach sensing element coupled to the circuit; wherein the breach sensing element is on a first side of the passivation layer and the substrate is on a second side of the passivation layer; a barrier configured to separate the breach sensing element from an ambient environment; wherein the breach sensing element is responsive to barrier damage; and wherein the instructions include, monitoring an output signal of the breach sensing element; and detecting a change in the output signal in response to barrier damage.

In another example embodiment, the monitoring instruction includes: monitoring at least one of a humidity level change or a photo current change in response to barrier damage.

In another example embodiment, in response to the barrier damage the instructions include at least one of: damaging the circuit; erasing a memory; transmitting an alert; placing the circuit into a decoy mode; or blowing a fuse.

In another example embodiment, the instructions include: distinguishing between barrier damage due to at least one of: a focused ion beam hole, a de-capping, a shear, a tear, an etch, or a physical attack.

In another example embodiment, the breach sensor includes a light sensor; and the instructions includes generating power with the light sensor in response to barrier damage.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

BRIEF DESCRIPTION OF THE DRAWINGS

FIG. 2 is an example breach of the sensor;

FIG. 3A is a first example layout of the breach sensor over or in a first circuit.

FIG. 3B is a second example layout of the breach sensor over or in a second circuit.

FIG. 4C is an example package breached by a focused ion beam (FIB).

Figure 1:
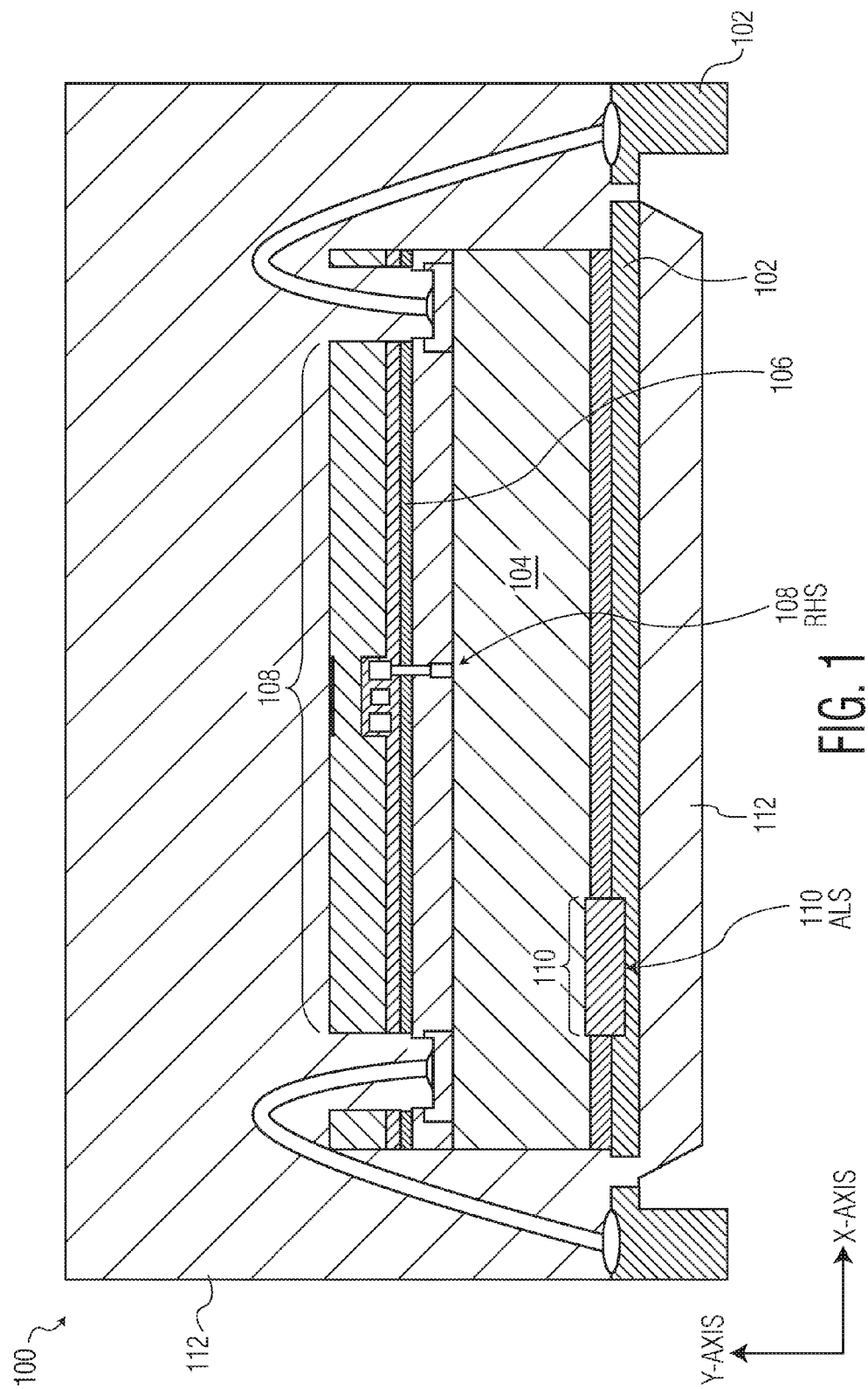
FIG. 1 is an example breach sensor.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Discussed herein are structures and techniques for detecting and alerting in response to both benign and not so benign package breaches. And, in the case of a not so benign breach, averting intentional physical hacking attacks designed to compromise various security features.

Structures include integrated circuit tampering detection structures based on relative humidity (RH) and/or ambient light (AL) sensors set to a first calibration state, such as by surrounding them with a barrier impervious to humidity and/or light, which then shift to a second calibration state in response to a breach in the barrier structure. Such structures permit distinguishing between various physical hacking attacks (e.g. a complete full package removal, and a local attack using FIB techniques) based on the RH and AL sensors' signal responses.

In response to a detected breach, additional alert and/or avert signals are selectively generated in various example embodiments.

FIG. 1 is an example breach sensor 100. In one example embodiment, the breach sensor 100 includes a lead-frame 102, a substrate 104 including an integrated circuit (not shown), a passivation layer 106, a first breach sensing element 108, a second breach sensing element 110, and a barrier 112.

In this example, the first breach sensing element 108 is a humidity sensing element 108 which functions as part of a humidity sensor and is coupled to the circuit. The humidity sensing element 108 is configured to detect a humidity level change in response to barrier 112 damage. The humidity sensing element 108 can be made of a polyimide and is coupled to a capacitive sensing structure and the integrated circuit so that a humidity reading may be monitored.

In an example embodiment, the first breach sensing element 108 is on a first side of the passivation layer 106 and the substrate 104 is on a second side of the passivation layer 106. The passivation layer 106 protects the integrated circuit in the substrate 104.

The humidity sensing element 108 in one example measures approximately 200×200 µm and is made in an extra metal layer on top of the passivation layer 106.

The second breach sensing element 110, in one example, is a light sensing element 110 which functions as part of a light sensor and is coupled to the circuit. The light sensing element 110 is configured to detect a light level change in response to barrier 112 damage. The light sensing element 110 can be made of a solar cell, an avalanche photodiode, or some other light sensitive device and is coupled to the integrated circuit so that a light level (e.g. photo current change) reading may be monitored.

The light sensing element 110 in one example is of a double diode configuration, created in a FEOL active area.

In other embodiments, the light sensing element 110 is configured to generate power in response to barrier 112 damage. The integrated circuit can be configured to receive this electric power thereby enabling various circuit functions which is further discussed below.

The first and second breach sensing elements 108, 110 can be formed respectfully on top of or as part of a CMOS device. In other embodiments the breach sensing elements 108, 110 could also be a gas sensor, or another capacitive sensing structure.

The barrier 112 is configured to separate the first and second breach sensing elements 108, 110 from an ambient environment. In FIG. 1, the barrier 112 is directly bonded to the first breach sensing element 108 and surrounds the second breach sensing element 110. The barrier 112 can be formed from an encapsulation material, a cover, a wrapper, a glue, a seal or other material.

The barrier 112 in one example is formed using a standard packaging encapsulant and can be applied using SO or QFN.

When covered by the barrier 112, the first and second breach sensing elements 108, 110 transmit reference signals to the integrated circuit.

However, when the barrier 112 is damaged the first and second breach sensing elements 108, 110 are able to respond to the ambient environment and the first and second breach sensing elements 108, 110 no longer transmit the reference signals to the integrated circuit. Instead the first and second breach sensing elements 108, 110 transmit new output signals that depend upon, for example, how much humidity and light is now reaching the first and second breach sensing elements 108, 110 from the ambient environment. The first and second breach sensing elements 108, 110 in one example embodiment are not calibrated due to a large difference between the reference signals and the new output signals.

This first and second breach sensing elements 108, 110 responsiveness corresponds to a "detection event", such as a focused ion beam hole, a de-capping, a shear, a tear, an etch, or a physical attack.

The detection event causes the integrated circuit in the breach sensor 100 to either generate an alert and/or enter one or more avert states.

Alerts establish a communication capability with an environment external to the breach sensor 100 (e.g. the outside world). Alerts can be interpreted in a variety of ways such as: a security breach, an SOS signal, an opening event, a changed operational state, an event completion, and so on. For example, if the alert corresponds to a security breach the alert can notify authorities, a manufacturer, an OEM, a networked environment, a bank, and/or others that the physical security of the device has been breached.

Example breach sensors 100 which also include an antenna coupled to the circuit can broadcast an alert over a much greater distance. In most cases the earlier such a security breach is detected and made known to the outside world, the better one can implement any damage control measures.

Avert states either alter circuits locally connected to the breach sensor 100 or cause remote servers to activate, deactivate, validate and/or invalidate devices and/or services monitored by the breach sensor 100. For example, in response to barrier 112 damage commensurate with a security breach, the breach sensor's 100 avert functionality can be configured to: switch off the normal chip operation, physically break a device, damage a circuit, erase a memory, enter a decoy mode, blow a fuse, and so on. Alternatively, in response to barrier 112 damage commensurate with an intended event, the breach sensor's 100 avert functionality can be configured to: switch on normal chip operation, activate a device, download data into a memory, and so on.

The detect, alert and avert circuits are in one embodiment powered by the light sensing element 110 even if the integrated circuit is disconnected from a power source (not shown). However in another example embodiment the power source is used by the detect, alert and avert circuits.

FIG. 2 is an example breach 200 of the sensor 100. In FIG. 2 a FIB hole 202 has been created in the barrier 112. The FIB hole 202 permits humidity 204 to reach the first breach sensing element 108. This changes a signal output by the first breach sensing element 108 resulting in a detection of the FIB hole 202. This detection, as mentioned above, can trigger various alert and avert events.

FIG. 3A is a first example layout 300 of the breach sensor 100 over or in a first circuit 302. The breach sensor cell 304 includes a set of breach sensing elements (e.g. the array pattern RH, AL, RH, AL, AL, RH, AL and RH shown in FIG. 3A).

In one example, the breach sensing elements are separated by a set of vertical barriers 306 laid out in such a way that selected breach sensing elements do not all respond to certain types of barrier damage and/or respond all at the same time. For example, in one example design a FIB hole over one relative humidity sensor does not trigger a detection event in another relative humidity sensor.

Such a configuration can provide useful information on which parts of the first circuit 302 have been breached, which may result in a different alert or avert response. Alternatively, such a configuration permits the set of breach sensing elements to have different reference states.

For example, one humidity sensing element can be pre-calibrated with a first humidity level, and a second humidity sensing element can be pre-calibrated with a second humidity level, different from the first humidity level. Such a design could detect barrier damage even in a controlled humidity environment.

FIG. 3B is a second example layout 308 of the breach sensor 100 over or in a second circuit 310. The array of breach sensing cells 312 include nine side-by-side cells which themselves include a set of breach sensing elements, such as described in FIG. 3A. This configuration fully covers the second circuit 310.

Figure 3C:
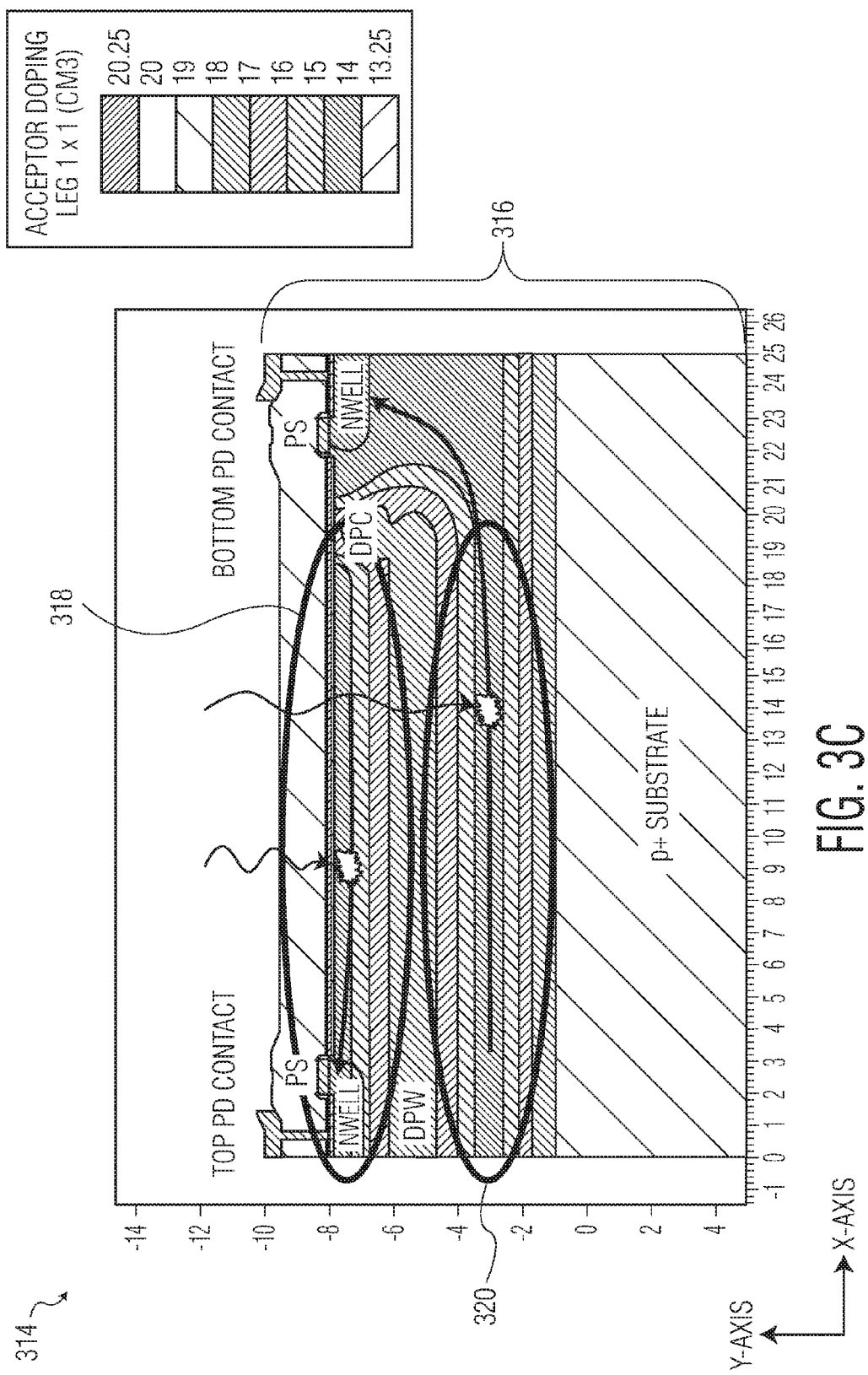
FIG. 3C is a third example layout of the breach sensor over or in a third circuit.

FIG. 3C is a third example layout 314 of the breach sensor 100 over or in a third circuit 316. This configuration includes a first breach sensing element 318 and a second breach sensing element 320 stacked underneath the first breach sensing element 318. In one example the first breach sensing element 318 is a diode closer to an external surface of the circuit 316 and that primarily is designed to detect visible light. The second breach sensing element 320 could then be a second diode buried within the circuit 316 and primarily designed to detect infrared light.

As shown by the examples in FIGS. 3A, 3B and 3C, the breach sensing element can easily be configured in size and shape so as to fit in either free circuit areas or wherever needed (e.g. above secure areas or at the periphery of a circuit).

Figure 4A:
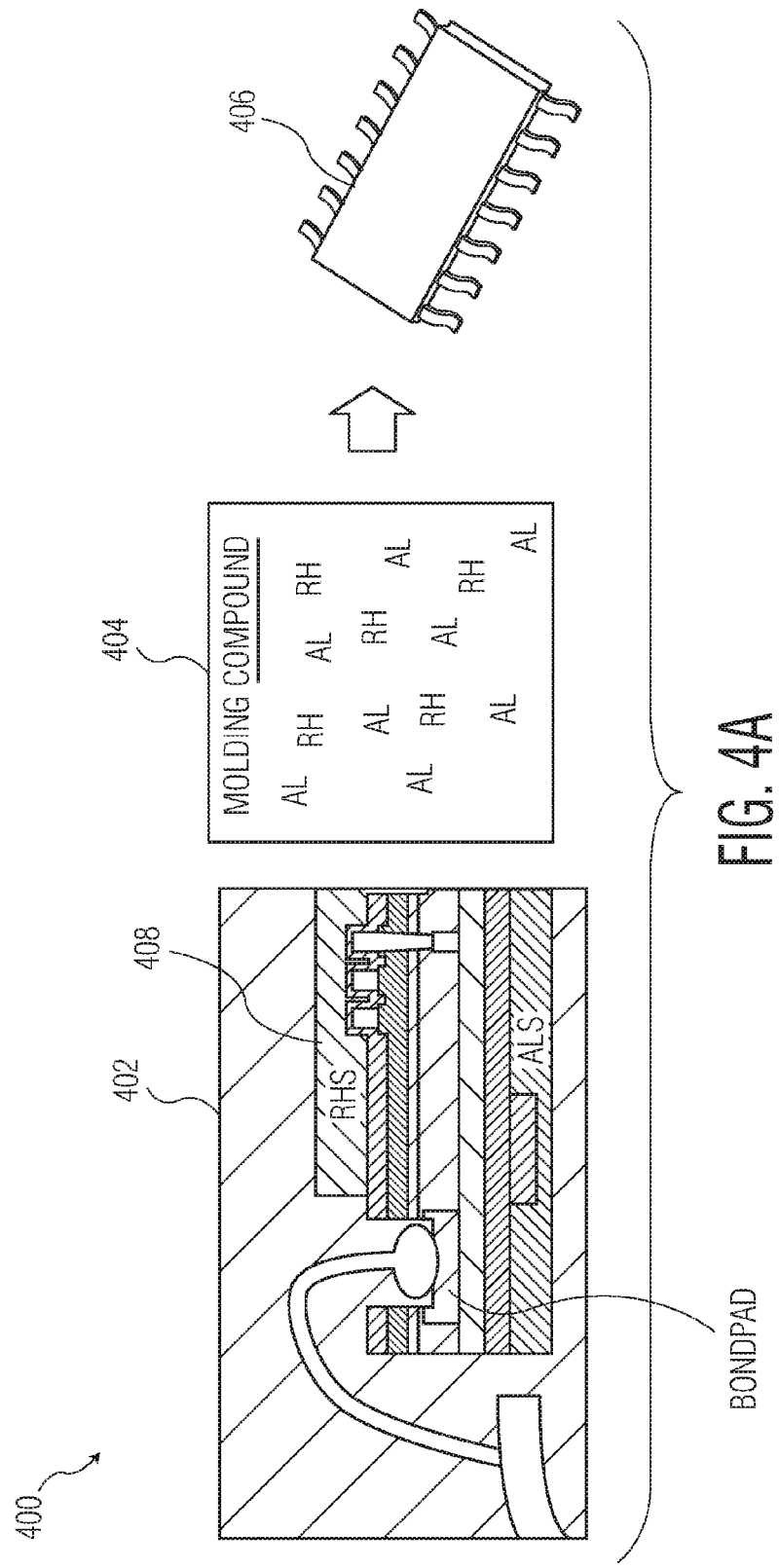
FIG. 4A is an example un-breached package.

FIG. 4A is an example un-breached package 400. The un-breached package 400 is shown in a first cross-sectional view 402, a second top-down view 404 and a third perspective view 406. The first cross-sectional view 402 shows one example relative humidity sensor (RHS), covered by a polyimide layer 408, and one ambient light sensor (ALS). The second top-down view 404 shows a pattern of ambient light (AL) and relative humidity (RH) sensors covered by a molding compound. The third perspective view 406 shows a finished package.

Figure 4B:
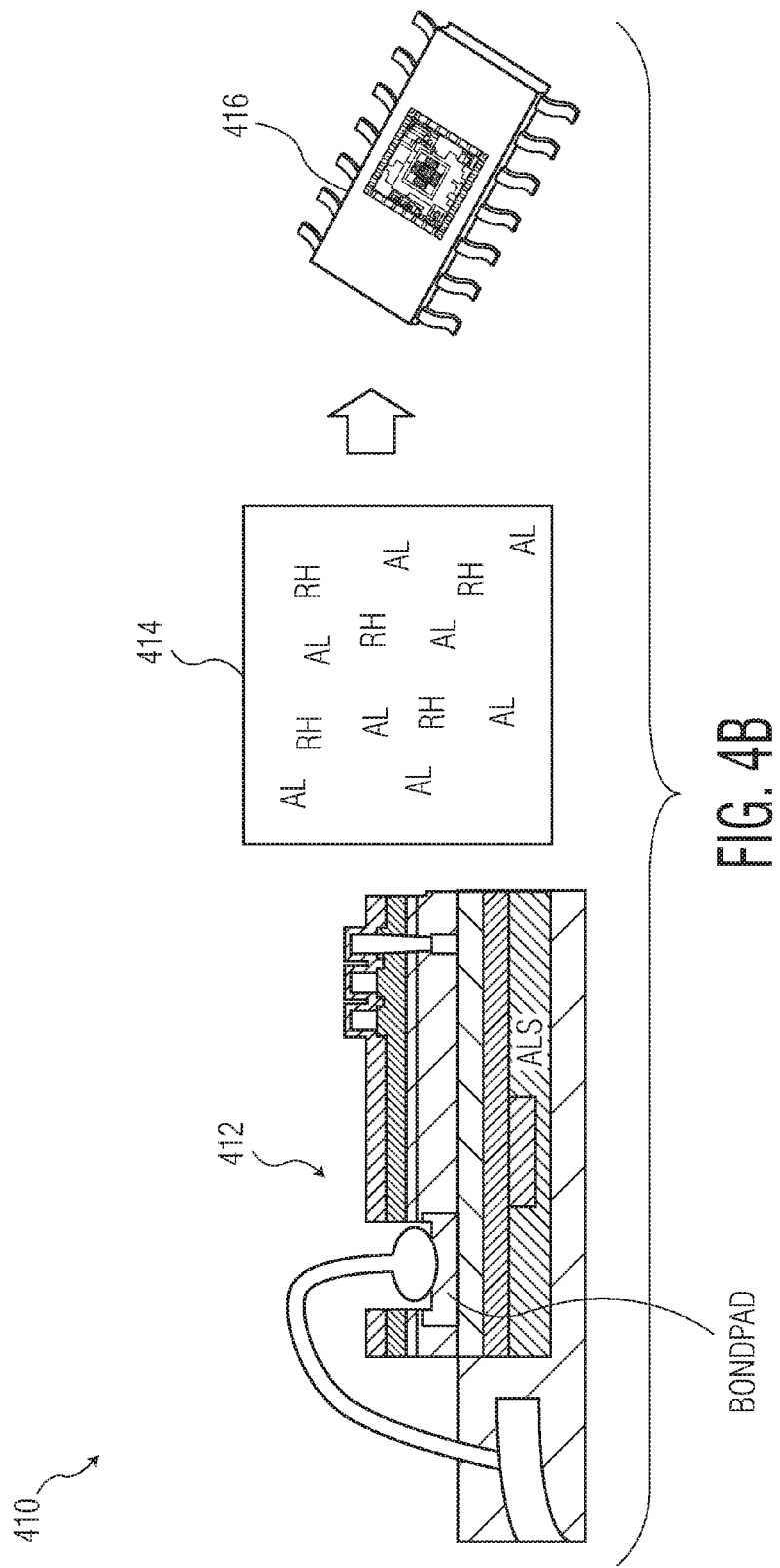
FIG. 4B is an example package breached by a full de-capping.

FIG. 4B is an example package 408 breached by a full de-capping. The de-capped package 410 is shown in a first cross-sectional view 412, a second top-down view 414 and a third perspective view 416. The first cross-sectional view 412 shows a fully exposed relative humidity sensor (RHS) with the polyimide layer 408 removed. This would cause a change in the relative humidity sensor's signal output, and the ambient light sensor (ALS) would also receive an increase in light intensity causing its output signal to change. The second top-down view 414 shows the exposed pattern of ambient light (AL) and relative humidity (RH) sensors with the molding compound removed. The third perspective view 416 shows the exposed chip package.

One example set of effects of a full de-capping is as follows. If the molding compound is completely chemically removed, then those chemicals will also remove the polyimide (of the RH sensor) which is present as a full layer. In this example it may not matter how many RH metal structures are present as the change in dielectric constant will be from approximately 3.5 towards ±1 which is enough to detect an intrusion a breach.

The de-capped RHS has a second capacitance lower than its first capacitance. Capacitance reduction in the RH structure as Polyimide is removed. Polyimide is removed, only (moist) air present. This generates a 2X-3X capacitance drop which can easily be spotted. This is a fairly steep step.

The AL sensor now has a second photo current greater than its reference first photo current. Photo current increases to levels>µA. Dark Current levels (sub-nA). Smaller sensor dimensions will give even larger effects.

FIG. 4C is an example package 418 breached by a focused ion beam (FIB) hole 422. The FIB-breached package 418 is shown in a first cross-sectional view 420 with the FIB hole 422, a second top-down view 424 and a third perspective view 426. The first cross-sectional view 420 shows the relative humidity sensor (RHS) exposed by the FIB hole 422. This would cause a change in the relative humidity sensor's signal output, and the ambient light sensor (ALS) would also receive an increase in light intensity causing its output signal to change. The second top-down view 424 shows the pattern of ambient light (AL) and relative humidity (RH) sensors with the molding compound breached by the FIB hole 422 which is closer to a particular set of AL and RH sensors. The third perspective view 426 shows the chip package exposed the FIB hole 422.

One example set of effects to a FIB-breached package 418 is as follows. The full layer polyimide is present everywhere. Fast diffusion will mean that moisture equilibrium will always reach the RH capacitor structure no matter how far away from the FIB hole 422. As the package is normally deposited at high temperatures (low moisture content), there will always be a delta RH that is large enough to be measured. Value of the un-breached RH capacitor can be stored at post-assembly test. If the FIB-breached package 418 is hooked up again then the new value can be compared to the original reference value (or to a reference cap in the interconnect).

The FIB hole 422 breached package 418 RHS sensor has a third capacitance greater than a first capacitance. The FIB hole 422 opens up the package molding compound to moisture and the polyimide layer is present everywhere with fast H2O diffusion. The change in capacitance will not be as dramatic as for full de-cap, but will be slightly more gradual. Contrary to the de-cap, the capacitance change will now be an increase in capacitance.

The FIB hole breached package 418 AL sensor has a third photo current greater than first photo current if the FIB hole 422 is close to buried photo sensor. Depending on the proximity of the AL sensor, an increase in photo current can be expected. The higher the photodiode density the better in that respect. If the FIB hole 422 is in the proximity of the AL sensor, the generated photocurrent will most probably give a large enough delta compared to the dark current. Smaller breach sending element dimensions will give even larger effects.

Figure 5:
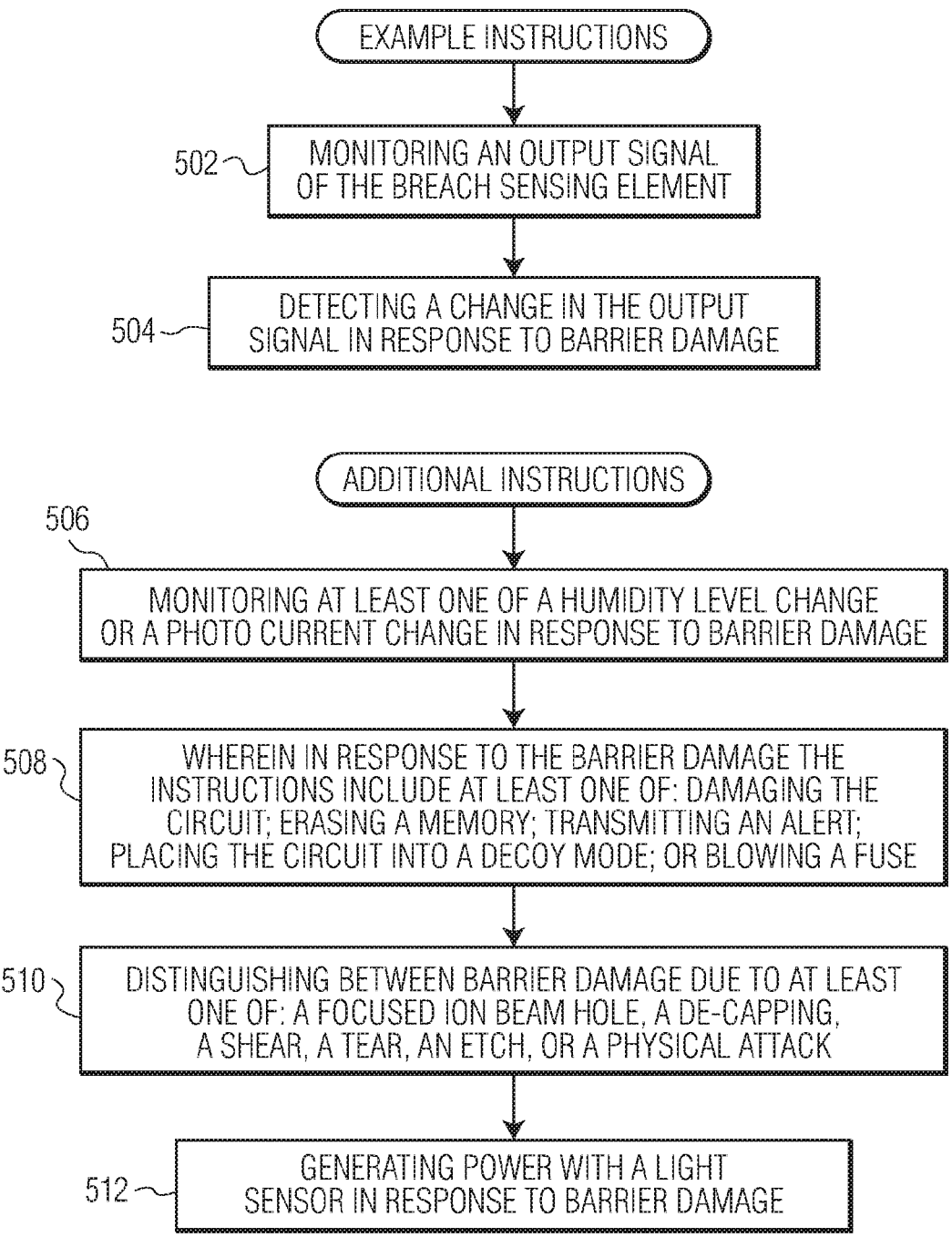
FIG. 5 is an example list of breach sensing and response instructions.

FIG. 5 is an example list of breach sensing and response instructions. The order in which the instructions are discussed does not limit the order in which other example embodiments implement the instructions unless otherwise specifically stated. Additionally, in some embodiments the instructions are implemented concurrently.

A first example instruction begins in 502, by monitoring an output signal of the breach sensing element. Next, in 504, detecting a change in the output signal in response to barrier damage.

The instructions can be augmented with one or more of the following additional instructions, presented in no particular order: 506—monitoring at least one of a humidity level change or a photo current change in response to barrier damage; 508—wherein in response to the barrier damage the instructions include at least one of: damaging the circuit; erasing a memory; transmitting an alert; placing the circuit into a decoy mode; or blowing a fuse; 510—distinguishing between barrier damage due to at least one of: a focused ion beam hole, a de-capping, a shear, a tear, an etch, or a physical attack; and 512—generating power with a light sensor in response to barrier damage.

Figure 6:
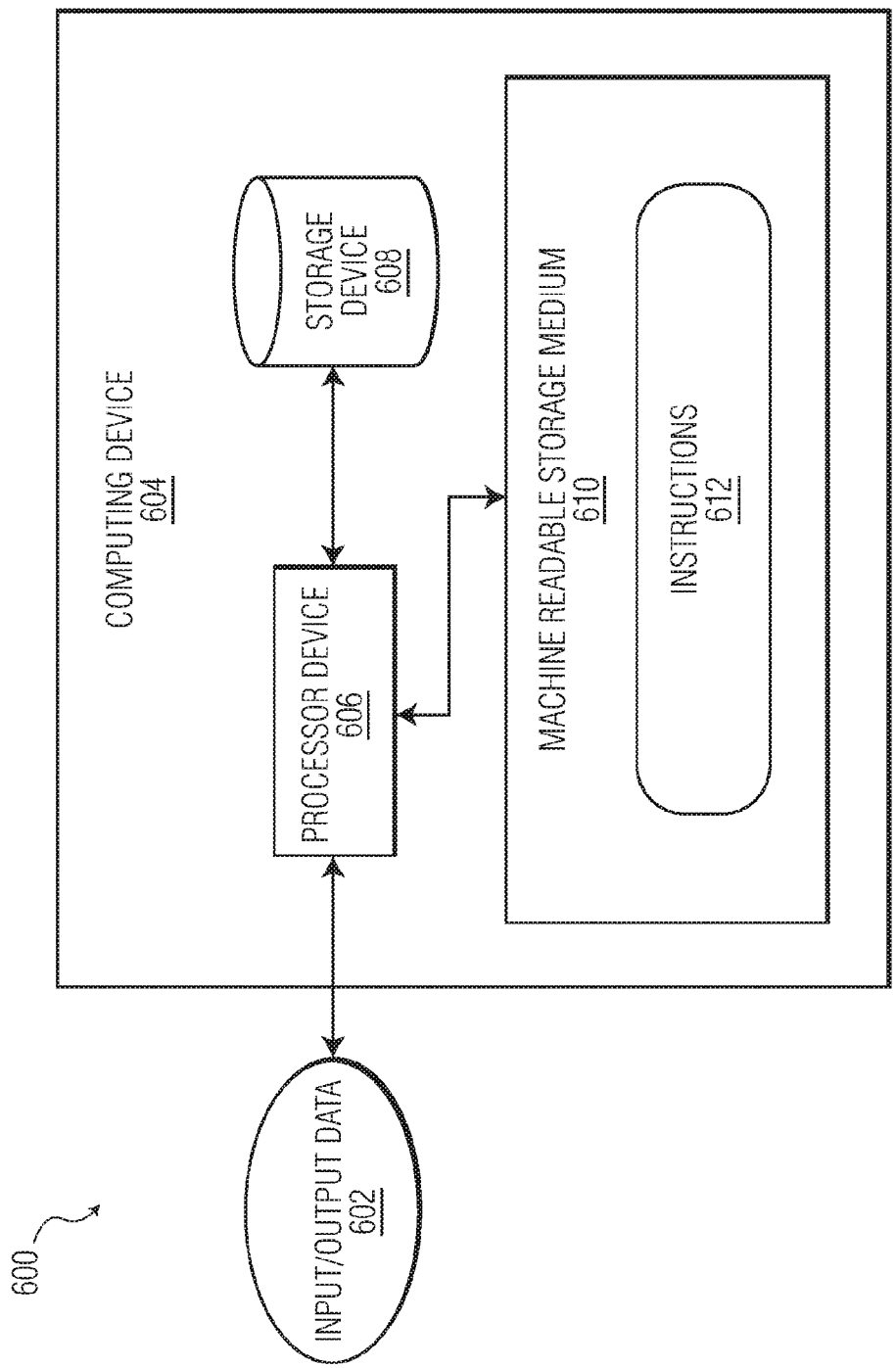
FIG. 6 is an example system for hosting the breach sensing instructions.

FIG. 6 is an example system for hosting the breach sensing instructions. The system 600 shows an input/output data 602 interface with an electronic apparatus 604. The electronic apparatus 604 includes a processor 606, a storage device 608, and a non-transient machine-readable storage medium 610. The machine-readable storage medium 610 includes instructions 612 which control how the processor 606 receives input data 602 and transforms the input data into output data 602, using data within the storage device 608. Example instructions 612 stored in the machine-readable storage medium 610 are discussed elsewhere in this specification. The machine-readable storage medium in an alternate example embodiment is a non-transient computer-readable storage medium.

The processor (such as a central processing unit, CPU, microprocessor, application-specific integrated circuit (ASIC), etc.) controls the overall operation of the storage device (such as random access memory (RAM) for temporary data storage, read only memory (ROM) for permanent data storage, firmware, flash memory, external and internal hard-disk drives, and the like). The processor device communicates with the storage device and non-transient machine-readable storage medium using a bus and performs operations and tasks that implement one or more instructions stored in the machine-readable storage medium. The machine-readable storage medium in an alternate example embodiment is a computer-readable storage medium.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. A breach sensor, comprising:
   a substrate including an integrated circuit;
   a breach sensing element coupled to the circuit;
   wherein the breach sensing element includes a light sensing element; and
   a barrier configured to separate the breach sensing element from an ambient environment;
   wherein the light sensing element is configured to capture light from the ambient environment admitted into the breach sensor in response to barrier damage;
   wherein the light sensing element is configured to generate power in response to the barrier damage; and
   wherein the integrated circuit is configured to operate on the power generated by the light sensing element.

2. The breach sensor of claim 1:
   wherein the breach sensing element includes a humidity sensing element configured to detect a humidity level change in response to barrier damage.

3. The breach sensor of claim 2:
   wherein the humidity sensing element is pre-calibrated with a first humidity level;
   further comprising a second humidity sensing element pre-calibrated with a second humidity level, different from the first humidity level; and
   wherein the first and second humidity sensing elements are separated by a second barrier.

4. The breach sensor of claim 2:
   wherein the humidity sensor includes at least one of: a capacitive sensing structure or a polyimide.

5. The breach sensor of claim 2:
   wherein the humidity sensing element position is offset laterally from the light sensing element.

6. The breach sensor of claim 5:
   wherein the breach sensor is configured such that barrier damage directly above the humidity sensing element is not detected by the light sensing element, and barrier damage directly above the light sensing element is detected by the humidity sensing element.

7. The breach sensor of claim 1:
   wherein the barrier is directly bonded to the breach sensing element.

8. The breach sensor of claim 1:
   wherein the barrier includes at least one of: a encapsulation material, a cover, a wrapper, a glue, or a seal.

9. The breach sensor of claim 1:
   wherein the barrier damage includes at least one of: a focused ion beam hole, a de-capping, a shear, a tear, an etch, or a physical attack.

10. The breach sensor of claim 1:
    wherein the light sensing element includes an avalanche photodiode.

11. The breach sensor of claim 1:
    wherein the circuit, in response to the barrier damage, is configured to at least one of: damage the circuit, erase a memory, transmit an alert, enter a decoy mode, or blow a fuse.

12. The breach sensor of claim 1:
    further comprising an antenna coupled to the circuit and configured to transmit a breach signal in response to barrier damage.

13. The breach sensor of claim 1:
    further comprising a second breach sensing element, proximate to the first breach sensing element; and wherein the two breach sensing elements are separated by a second barrier configured to separate the second breach sensing element from the first breach sensing element.

14. The breach sensor of claim 13:
wherein the two breach sensors are at least one of: stacked or side-by-side.

15. The breach sensor of claim 1:
further comprising a passivation layer coupled to the substrate;
wherein the breach sensing element is on a first side of the passivation layer and the substrate is on a second side of the passivation layer.

16. An article of manufacture including at least one non-transitory, tangible machine readable storage medium containing executable machine instructions for breach sensing, comprising:
wherein the article includes,
a substrate including an integrated circuit;
a breach sensing element coupled to the circuit;
wherein the breach sensing element includes a light sensing element;
a barrier configured to separate the breach sensing element from an ambient environment; and
wherein the instructions include,
monitoring an output signal of the breach sensing element;
detecting a change in the output signal in response to barrier damage;
capturing light from the ambient environment, admitted into the breach sensor in response to barrier damage, with the light sensing element;
generating power in response to the barrier damage, with the light sensing element; and
operating the integrated circuit on the power generated by the light sensing element.

17. The article of claim 16, wherein the monitoring instruction includes:
monitoring at least one of a humidity level change or a photo current change in response to barrier damage.

18. The article of claim 16, wherein in response to the barrier damage the instructions include at least one of:
damaging the circuit;
erasing a memory;
transmitting an alert;
placing the circuit into a decoy mode; or
blowing a fuse.

19. The article of claim 16, wherein the instructions include:
distinguishing barrier damage due to at least one of: a focused ion beam hole, a de-capping, a shear, a tear, an etch, or a physical attack.

* * * * *